US006404851B1

(12) United States Patent
Possin et al.

(10) Patent No.: US 6,404,851 B1
(45) Date of Patent: Jun. 11, 2002

(54) METHOD AND APPARATUS FOR AUTOMATIC EXPOSURE CONTROL USING LOCALIZED CAPACITIVE COUPLING IN A MATRIX-ADDRESSED IMAGING PANEL

(75) Inventors: George Edward Possin, Niskayuna; Robert Gideon Wodnicki, Schenectady; Sung Su Han, Niskayuna, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/537,485

(22) Filed: Mar. 30, 2000

(51) Int. Cl.[7] .................................................. H05G 1/38
(52) U.S. Cl. ...................... 378/98.7; 378/98.8; 378/108
(58) Field of Search ............................... 378/98.7, 98.8, 378/108; 250/370.09

(56) References Cited

U.S. PATENT DOCUMENTS

| | | | |
|---|---|---|---|
| 5,040,041 A | 8/1991 | Yamada et al. ............. 257/222 |
| 5,194,736 A | 3/1993 | Meulenbragge et al. ...................... 250/370.07 |
| 5,340,988 A | 8/1994 | Kingsley et al. ........ 250/370.09 |
| 5,401,668 A | 3/1995 | Kwasnick et al. ............ 438/69 |
| 5,485,501 A | 1/1996 | Aichinger .................. 378/98.7 |
| 5,574,765 A | 11/1996 | Hassler et al. ............. 378/98.7 |
| 5,585,638 A | 12/1996 | Hoffman ................ 250/370.07 |
| 5,587,591 A | 12/1996 | Kingsley et al. .............. 257/59 |
| 5,610,403 A | 3/1997 | Kingsley et al. ........ 250/370.09 |
| 5,610,404 A | 3/1997 | Possin .................... 250/370.09 |
| 5,648,654 A | 7/1997 | Possin ..................... 250/208.1 |
| 5,751,783 A * | 5/1998 | Gransfors et al. ........... 378/108 |
| 5,869,837 A | 2/1999 | Huang .................... 250/370.09 |
| 5,877,501 A * | 3/1999 | Ivan et al. .............. 250/370.09 |
| 5,937,027 A | 8/1999 | Thevenin et al. ........... 378/98.8 |
| 6,243,441 B1 * | 6/2001 | Zur ............................ 378/98.8 |

FOREIGN PATENT DOCUMENTS

| | | |
|---|---|---|
| EP | 817472 A1 | 1/1998 |
| EP | 1001665 A | 5/2000 |
| FR | 2771513 A | 5/1999 |

OTHER PUBLICATIONS

International Search Report

* cited by examiner

*Primary Examiner*—Drew Dunn
*Assistant Examiner*—Therese Barber
(74) *Attorney, Agent, or Firm*—Donald S. Ingraham; Christian G. Cabou (57) ABSTRACT

A method and system for an automatic exposure control (AEC) arrangement for a matrix-addressed imaging panel having an array of sensors including use of localized regions of the imaging panel exhibiting capacitive coupling. In one embodiment, the matrix-addressed imaging panel includes one or more AEC electrode receptive field regions that provide a signal representative of exposure specific, respective AEC electrode receptive field regions. Additionally, in another embodiment, the imaging array includes data line signal monitoring regions in which capacitive coupling between electrodes in radiation sensors adjacent to the data line are read and processed to provide and AEC signal. In another embodiment, the imaging array includes both AEC electrode filed receptive regions and data line signal monitoring regions that are coupled to an AEC controller for control of the radiation source for the imaging array.

29 Claims, 6 Drawing Sheets

METHOD AND APPARATUS FOR AUTOMATIC EXPOSURE CONTROL USING LOCALIZED CAPACITIVE COUPLING IN A MATRIX-ADDRESSED IMAGING PANEL

BACKGROUND OF THE INVENTION

The present invention relates to an exposure control arrangement for a matrix-addressed imaging panel. More specifically, a matrix-addressed imaging panel using localized regions of capacitive coupling as a control, to infer an x-ray dose absorbed by an imaged subject to effect automatic exposure control (AEC).

Matrix-addressed x-ray imaging panels composed of semiconductor thin film transistors (TFTs) and radiation sensors have many useful applications in the fields of medicine and industrial inspection. Typically, such solid state imaging systems use a two dimensional matrix of radiation sensors and readout devices to convert radiation into digital signals corresponding to the incident radiant energy. In radiation imaging systems used in medical applications, radiation energy passing through, or emanating from, a patient's body is detected and imaged.

When imaging energy from an imaging energy source is applied to a subject to be imaged, which may be a human or animal patient, or an inanimate part, portions of the imaging energy are blocked by the subject and remaining portions are transmitted through the subject and impinge on the imaging device. Typically this energy is converted to electrical charge or voltage either directly in an array of direct radiation sensors or indirectly using a scintillator which converts the energy to light which is converted to charge or voltage by an arrays of photo sensors such as a photodiodes. The amount of charge is advantageously proportional to the amount of absorbed radiation energy incident on the detector. Each sensor is connected via a corresponding controlled switch (e.g., TFT) to a corresponding data line. Each controlled switch is operable from a scan line, which is controlled by a scan line controller, to selectively pass an output signal from the corresponding sensor to its associated data line. The controlled switches are selectively closed, one at a time, to pass the output signals to the data lines. Each data line is read and integrated by a respective read-out amplifier. The separate integrated sensor values are processed and assembled to form an image representation of the subject when viewed on a display device.

It is desirable to have real time readout of the accumulated X-ray dose or signal in a panel of sensors sensing X-ray doses during exposure of an object (such as a person who is a medical patient) being imaged. Such a measure of accumulated dose is used to determine when the desired exposure level has been reached such that the X-ray tube can then be turned off. The desired exposure depends on factors such as the characteristics of the imaging system (e.g., need to avoid saturation), the characteristics of the object being imaged (e.g., in the case of a patient, the dose suitable under the best medical practice), or both factors. The method of turning off the X-ray tube based on the accumulated X-ray dose measurement is typically called automatic exposure control (AEC).

In one type of imaging system, the AEC includes one or more dedicated radiation sensors positioned below a detector (e.g., outside of an imaging panel) or film cassette. Signal generated by X-rays absorbed in the active volume of the sensor are used to infer the dose absorbed by the imaged object or by the imaging device. This method suffers from a number of disadvantages, including increased system cost and complexity (for the dedicated exposure control components), and the difficulty of calibrating the system (with the exposure control sensors separate from the imaging panel or film) to correlate the signal generated by the radiation sensor with the absorbed dose in the detector or object.

It is desirable to have a robust and effective system by which to sense imager panel saturation, and that system also desirably does not adversely affect the complexity, cost, or operating characteristics of the imaging panel. Such a system also desirably is readily calibrated.

It is further advantageous to use values representing a localized reading of instantaneous panel exposure to imaging radiation, as an input to a calculation of accumulated imaging energy dose, thus providing the basis for controlling total imaging radiation dose.

SUMMARY OF THE INVENTION

In one embodiment of this invention, an imaging system includes a matrix-addressed imaging panel having a plurality of pixels, each of which comprises a respective radiation sensor. Each pixel further comprises at least one respective pixel readout switch disposed to selectively couple the pixel radiation sensor to a respective data line in the imaging panel for purposes of reading the image information. At least one data line exposure signal, derived from at least one exposure-monitoring data line in the imaging panel, is coupled to an exposure controller. During this mode of operation the system is configured to sense a capacitively-coupled data line exposure signal from at least one radiation sensor capacitively-coupled to the exposure-monitoring data line. The data line exposure signals are processed by the exposure controller to provide a panel exposure signal corresponding to incident radiation sensed during an exposure control period when the respective pixel readout switches for the exposure-monitoring data line are in an electrically open condition.

In one embodiment of this invention, a method of operating an imaging system having a matrix-addressed imaging panel having a plurality of radiation sensor pixels, each pixel radiation sensor being connected via a respective pixel readout switch to a respective data line, includes the steps of: sensing exposure signals appearing on at least one data line from at least one radiation sensor with the pixel readout switches open; and generating a panel exposure signal based on the data line exposure signals generated during the periods when the pixel readout switches on a data line are in a non-conductive condition. The exposure signals that appear on the data lines via capacitive coupling of the photodiodes to the data lines and are sensed by an exposure controller configured to generate a real-time panel exposure signal that typically is used as a control input for the imaging energy source.

In another embodiment of the invention, a method and system for an exposure control arrangement for a matrix-addressed imaging panel comprises at least one Automatic Exposure Control (AEC) signal line disposed in a respective localized region of an imaging panel so as to provide a respective AEC receptive field region defined by the pixel diode electrodes which are disposed vertically adjacent to the AEC electrode. The AEC line in turn is coupled to an external amplifier to generate a localized exposure signal for use with panel exposure control.

In a still further embodiment of this invention, an imager comprises both the coupling for the data line exposure signal and also at least one AEC electrode as described above.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
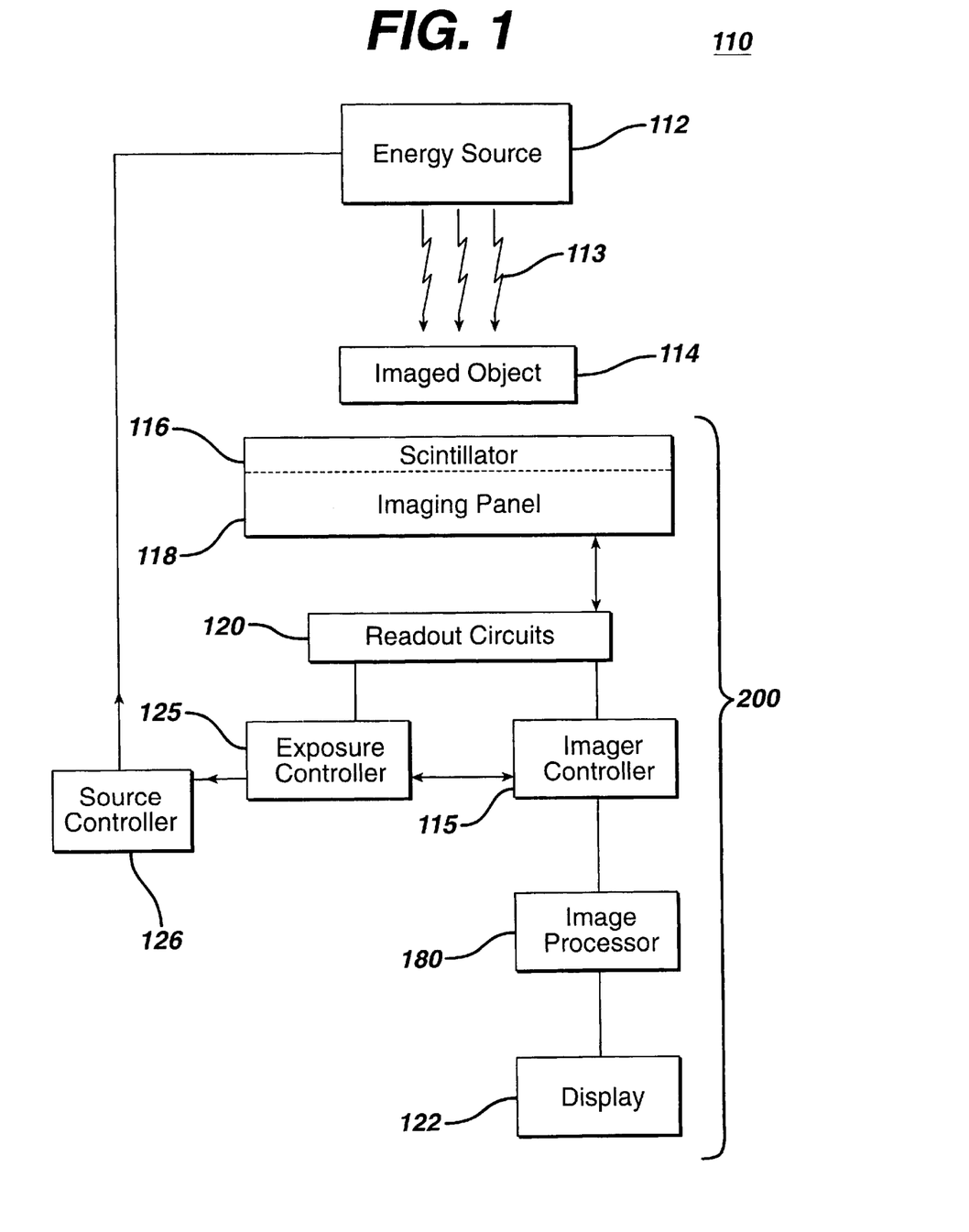
FIG. 1 is a simplified block diagram of a radiation imager in accordance with an embodiment of the present invention.

A radiation imager 110 in accordance with the present invention comprises a radiation imaging energy source 112 disposed to illuminate an object 114 to be imaged with radiation energy 113. Radiation energy 113 passing through object 114 is sensed in a radiation detector 200 that comprises an imaging panel 118, readout circuits 120, an imager processor 115, and an exposure controller 125. Exposure controller 125 and imager controller 115 are coupled to a source controller 126 that controls the state of energy source 112; image processor 180 is also coupled to a display 122 for presenting image data generated by imager 110.

Imaging panel 118 typically comprises a matrix-addressed array of pixels (described in greater detail below), each of which comprises a respective radiation sensor. "Matrix-addressed" refers to rows and columns of pixels, each coupled to a respective data line and to a respective control line (often referred to as a "scan" line in the digital imager art) so that data from pixels can be selectively readout by controlling electrical coupling of the radiation sensors to their respective data lines. Each pixel further comprises at least one respective pixel readout switch disposed to selectively couple the pixel radiation sensor to a respective data line in the imaging panel. When operating, the imager is controlled during an exposure cycle to provide a collection period when the pixels are electrically disconnected from the respective data lines while collecting charge corresponding to the incident radiation flux, and a readout period when the pixel radiation sensor is electrically connected to the data line to enable the data to be collected by the readout electronics circuits coupled to the panel.

Exposure controller 125 is configured to control source controller 126 (and hence the illumination of object 114 with radiation 113) during operation of the imager 110, as detailed below. As used herein, "adapted to", "configured" and the like refer to computational and control devices (such as programmable computing devices and application specific integrated circuits) that are programmed to generate an output (e.g., a control signal) in correspondence with one or more input signals. "Exposure control," as used herein, refers to monitoring exposure (or dose) of radiation 113 incident on at least a portion of imager panel 118, in particular during the collection period of the imaging readout cycles when the pixel radiation sensors in imager panel 118 are not directly connected (that is, not connected via the respective pixel readout switch) to the data lines. In embodiments of this invention, the sensing of exposure during the collection period is done with the radiation sensors and matrix-address lines (e.g., data lines) already in the imager panel, without the need for separate radiation sensors dedicated for exposure control monitoring.

Sensing exposure during these collection periods is desirable for several reasons. For example, radiation exposure of the imaged object 114 is a factor when imaging a human or animal subject as medical considerations dictate tracking exposure such that overexposure to X-rays is avoided. Further, image quality can be degraded if the exposure is too high so that panel 118 may fail to provide desired information as too many of the radiation sensors will be in saturation. Additionally, proper imaging requires at least a minimum level of exposure to generate useful image information such that tracking exposure can also be used to ensure that sufficient radiation energy is applied.

Alternately the radiation sensors may comprise a thick layer of semiconductor which can directly convert radiation from the energy source 112 to an electrical charge. These devices are so called direct semiconductor x-ray sensors. As used herein, "radiation sensor" and the like is used in its broadest sense to denote means by which the incident radiation used for imaging is detected and converted to a corresponding electrical signal. By way of example and not limitation an arrangement using a photo sensor array is described herein.

Imaging panel 118 typically further comprises a scintillator 116 that is optically coupled to the array of semiconductor radiation sensors in imaging panel 118. In such an arrangement, the radiation sensors typically comprise photosensors, such as photodiodes or the like. In operation, the incident radiation (such as x-rays) is predominantly absorbed in the scintillator layer (comprising, e.g., cesium iodide or the like), resulting in the generation of optical photons, which in turn are detected by the photosensor array. The exposure control modalities of the present invention can also be used with alternative embodiments of a radiation imaging panel, such as detectors comprising direct conversion devices (that is, devices that directly convert incident radiation (such as x-rays) to electrical charge without use of a scintillator).

Figure 2:
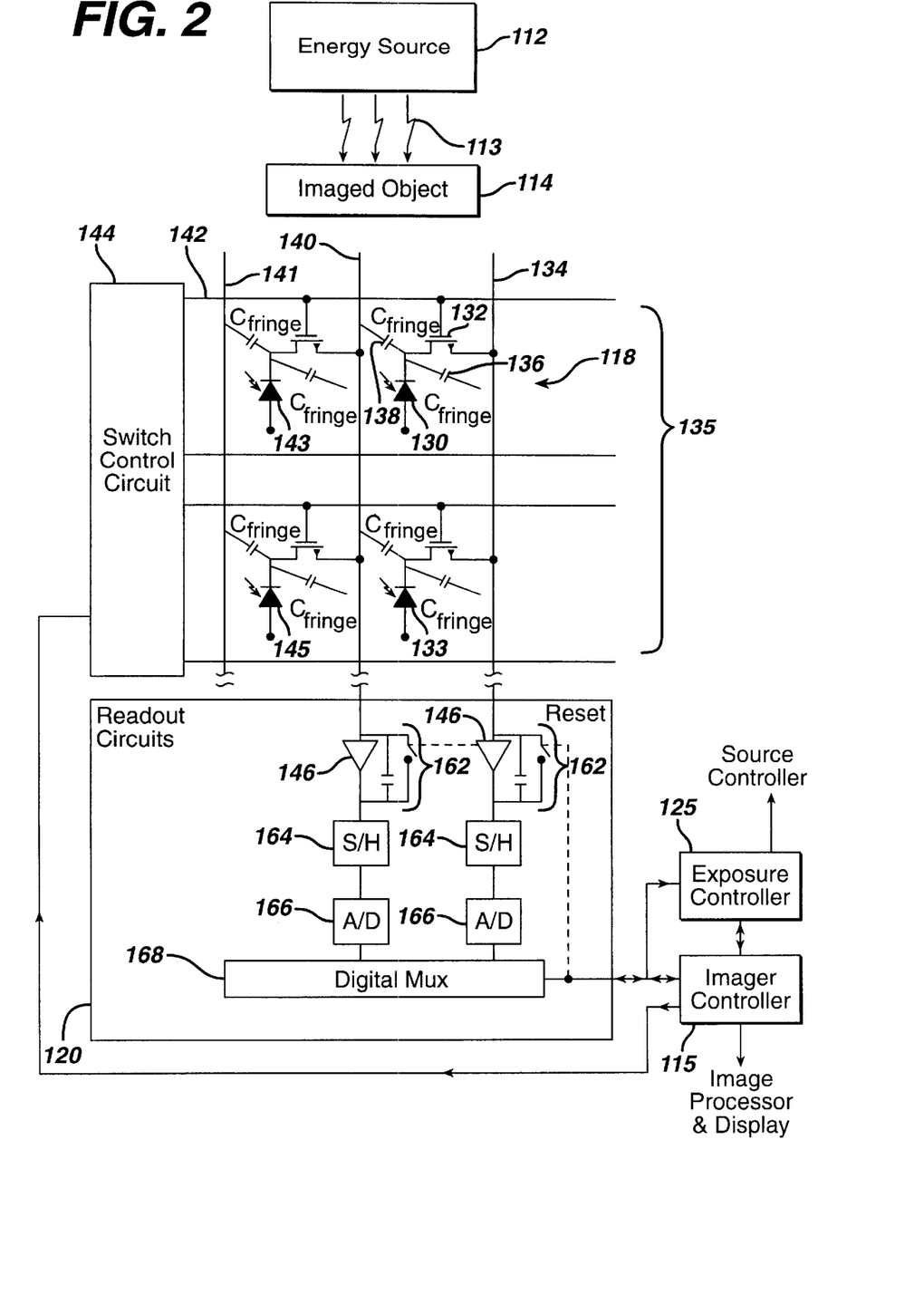
FIG. 2 is a combined simplified block diagram and schematic of the imaging system according to an embodiment of the present invention.

One embodiment of the present invention in imaging system 110 is illustrated in FIG. 2. By way of illustration and not limitation, radiation energy source 112 comprises an x-ray tube and imaging panel 118 comprises a scintillator 116 (not illustrated in FIG. 2) coupled to a photosensor array 135.

Photosensor array 135 in panel 118 comprises a plurality of rows and columns of semiconductor components (such as representative photodiode 130 and associated readout switch 132), only some of which are labeled for ease of illustration. Photodiodes 130 are selectively connected by pixel readout switches, such as thin film field effect transistors ("FETs") 132 to corresponding data lines 134, which lines are shown extending vertically in FIG. 2, thereby defining columns in the array of panel 118. Alternatively, diodes can be used in some arrangements to provide the pixel switching function of the FETS. It will be appreciated that FIG. 2 only shows a few columns and a few rows of the array, but a quite large number of columns and rows are used in an actual imaging panel 118.

For purposes of illustrating one embodiment of the present invention, a parasitic fringing capacitance 136 that capacitively couples a given photodiode 130 to its corresponding data line 134 and a similar fringing capacitance 138 that capacitively couples a given photodiode 130 to an adjacent data line 140 (i.e., this data line corresponds to a photodiode in an adjacent column) is shown in FIG. 2. As used herein, "fringing capacitance," "parasitic capacitance" and the like refers to the capacitive coupling between components in the array, such as data lines and diode electrodes, that are electrically insulated from one another in the array design. The present invention uses the normally undesirable fringing capacitance as a source of signals for the exposure control system, thereby lowering the cost and complexity of an imaging system.

Each row of switches 132 has a corresponding scan or control line 142 (typically referred to as a scan line, shown extending horizontally in FIG. 2) responsive to switch control circuit 144 in order to close all switches in a given row (corresponding to a respective control line 142) at a time in the image readout cycle to enable readout via the respective data lines 134 of radiation sensors 130 along that row.

Data lines 134 are coupled to readout circuits 120 that collect the electrical signals from the panel and distribute these signals to controller 115 and image processor 180. Readout circuits 120 comprise a plurality of integrating amplifiers 146 coupled to the data lines; a typical arrangement, as is illustrated in FIG. 2, a respective amplifier 146 is coupled to each data line. A respective reset circuit 162 is coupled to each amplifier 146 to enable resetting the amplifier to a known condition prior to charge integration for image or exposure signal readout. Each amplifier 146 is further coupled to a respective sample and hold circuit 164 that measures the total charge received (which corresponds to the voltage out of the charge amplifier) by the respective amplifier 146 to which it is coupled. The signal generated by S/H circuit 164 is coupled to a respective analog-to-digital converter 166 and thence to a digital multiplexer 168 for further distribution to controller 115 and display 180.

Exposure controller 125 is adapted to receive exposure signals from at least one amplifier 146 coupled to at least one data line in imager panel 118; typically a plurality of data lines are used to monitor exposure, and most commonly, all data lines in imager panel 118 are used (the particular lines monitored for exposure control can be selected, for example, by control signals applied to digital multiplexer 168). Controller 125 is configured to generate a panel-exposure signal in correspondence with the at least one exposure signal received from imager panel 118; this panel-exposure signal is further used to generate a control signal (when a selected exposure level has been met) that is coupled to source controller 126 to cause energy source 112 to cease irradiating imaged object 114.

Commonly, each data line in imager panel 118 is coupled, via readout circuit 120, to exposure controller 125. In a further embodiment, a selected grouping of data lines less than the total number of data lines in the panel (e.g., a group such as data lines 134, 140, 141 in FIG. 2) are coupled to exposure controller 125 so that signals from these data lines are used to generate the panel exposure signal. The choice of data lines to be coupled to exposure controller 125 can be accomplished selectively with digital multiplexer 168. Thus, for example, depending upon the object being imaged, the operator of imager 110 (or alternatively, a program in controller 115) can select an appropriate model of exposure areas of interest on the panel 118. Exposure areas of interest refer to areas where, because of the nature of the imaged object 114, the measured exposure during the exposure readout cycle will provide a good sample to use determine the appropriate period of irradiation of the imaged object, as discussed in more detail below.

In a normal image read cycle, for a single scan line, the respective charge amplifiers 146 are reset to a known condition. In the example circuit in FIG. 2, reset consists in part of closing switch 162 for a period of time and then opening switch 162. Readout of signal for image generation is commenced via image controller 115 and switch control circuit 144 to turn on (that is, cause the FETs to become conductive) the respective pixel readout switches (e.g., switch 132) on a given scan line(e.g., scan line 142); this condition enables the charge accumulated on sensor 130 during the exposure period to be transferred to the respective charge amplifier 146 coupled to the respective data line (e.g., line 134). The scan line is then controlled (by signals from switch control circuit 144) to the off condition, and the charge received by amplifier 146 is transferred to S/H circuit 164 and thence to A/D circuit 166, and ultimately to multiplexer 168. The typical time to complete one readout function for a single line is in the range between about 30 microseconds to about 100 microseconds.

In the Automatic Exposure Mode of operation, all scan lines are controlled to be in the "off" state so that no sensors are directly coupled their respective data lines. Then the energy source 112 is turned on. In this mode, with the charge amplifiers 146 reset to a known condition, the charge that is capacitively coupled to each data line continuously transfers to the respective amplifier 146 coupled to that data line. The charge received by the amplifier since the last reset (e.g., start of a cycle) is captured by sample and hold S/H circuit 164 and A/D circuit 166 at some desired time determined by the exposure or image controller. This reading operation can be repeated multiple times. These signals from respective data lines received by digital multiplexer 168 are coupled to exposure controller 125. The amplifier is typically reset multiple times during the monitoring of each radiation exposure from energy source 112. A single reset cycle per exposure is possible but typically the charge level induced on the data line will exceed the maximum signal capacity of the amplifier. Each time the amplifier is reset the last reading before reset is stored in the image controller and summed with subsequent readings. This sum of signals representing accumulated capacitively coupled charge detected on a data line is generated; this sum signal represents accumulated dose for the data lines monitored and is used to generate a control signal to cease radiation exposure of object 114 at a given accumulated dose. Each x-ray exposure is typically in the range between about 0.1 second and 10 seconds.

By way of example and not limitation, imager 110 can be used to image an abdomen in a human. If the imager is aligned such that the data lines are approximately parallel to the long axis of the person being imaged, the pixels in imager panel 118 in the central region of the panel underlie thick regions of the body. In this situation, the x-ray signal per pixel in the central region of the abdomen is proportional to the total signal divided by the number of pixels attached to that data line, and the magnitude of the x-ray exposure can be calculated as outlined below.

In another example, imager 110 can be used for mammography. In this arrangement, the exposure area of interest is in the central region of image representing most of the breast. Because the breast is compressed to a constant thickness, the x-ray exposure to the imager is similar under most of the breast. From the spatial variation of the signal from the data lines the shape of the breast can be estimated.

This shape information can be used to infer the fraction of the pixels covered by breast tissue for each data line. In particular, near the chest wall most or all of the pixels will be covered. For a CC (that is, top) view, typically about 75% of the pixels in the panel underlie tissue; for a lateral view, typically all pixels are covered in most (about 75%) of clinical cases. For the central regions of the imager, underlying the mass of tissue, the x-ray exposure per pixel corresponds to the signal detected on an exposure monitoring data line divided by the number of pixels on that data line. When some number of the pixels on a data line are not covered by tissue, one will have a much higher signal and the signal due to the uncovered pixels must be subtracted from the total data line signal to give a value representative of the exposure in the tissue-covered region. The signal to be subtracted in this latter case can be estimated from a model which estimates the number of uncovered pixels; this procedure suffers increasing accuracy when the number of uncovered pixels on a data line increases. Alternatively, and x-ray opaque material (for example a metal such as tungsten or copper with thickness of about 1 mm) can be inserted up to the tissue overlying the imager panel so as to reduce the number of uncovered pixels.

A radiation imager comprising exposure controller 125 in accordance with the present invention utilizes the radiation sensors in imaging panel 118 as the source for exposure signals to calculate exposure. This arrangement obviates the need for sensors separate from the panel to determine exposure and also obviates the need for a calibration process to correlate detected radiation at an off-panel sensor with the radiation incident on the detector panel.

A better appreciation of the operation of exposure controller 125 can be obtained with a more detailed review of characteristics of the panel 118. The cathode side of diode 130 is capacitively coupled to a respective exposure monitoring data line 134 (that is, the data line to which diode 130 is coupled via respective pixel readout switch 132) and an adjacent exposure monitoring data line 140 (that is, the data line to which an adjacent diode 143 in that row of diodes is coupled via its respective pixel readout switch). The magnitude of this parasitic coupling capacitance $C_{fringe}$ varies with the panel structure. Typically, it is in the range of 0.2 to 0.7 pF/cm or 0.002 to 0.007 pF/pixel for 100 micron pixels. The potential at the cathode of diode 132 changes as the panel 118 is struck by X-rays. Some of this charge is capacitively coupled to the data line 134. The ratio of this coupled charge signal to the charge induced on the diode is given by:

$$C_{fringe}/C_{diode} \sim 0.005/0.5 = 0.01, \text{ or } 1\%$$

where $C_{diode}$ is the capacitance of the diode 130.

The signals from all diodes in a given column of pixels couples to their respective data line (e.g., data line 134 for photodiodes 130, 133, and others (not shown) in that column of the array) and to their adjacent data line (e.g., data line 140 for photodiodes 143, 145, and others (not shown) in that column of the array). For a typical panel used in mammography, there are about 2300 diodes per data line ($N_d$) and the coupling occurs for diodes on each side. Therefore, there is twice that number or 4600 diodes, coupled to each exposure monitoring data line. The coupled signal on a given data line (other than data lines at the edge of the imager panel, where diodes are only on one side of them) is about 46 times ($0.01 \times (2\ N_d) = 46$) the accumulated charge on a single pixel, if all the pixels are illuminated equally.

The readout amplifiers 146 amplifiers (also referred to as charge amplifiers) are coupled to each data line in imager panel 118 to provide the pixel readout signal during the image readout process. These same amplifiers are used to detect the charge induced on the data lines during the collection portion of the readout cycle and provide this information to exposure controller 125. This combined use of readout amplifiers 146 is accomplished by modifying the readout timing normally used during the imaging process. The minimum charge integration time of a typical solid state radiation imager readout amplifier design is about 30 $\mu$secs. Longer charge integration times are easily achieved and can be controlled by signals from the imager or exposure controller. The maximum rate of charge generation in each pixel diode is about 3 pC/sec and the amplifier saturates at about 5 pC, depending on the gain range. Integrating the charge induced on a given signal line for a relatively short exposure time of 8000 $\mu$secs would yield a signal of about:

$$(8000\ \mu secs)(3\ pC/sec)(46) = 1.1\ pC$$

The readout amplifiers 146 are controlled to perform integration during substantially the entire time of irradiation of the object 114 and integrate signals from each exposure monitoring data line coupled (via readout circuits 120) to exposure controller 125. Exposure controller 125 typically is configured to provide a quasicontinuous readout of average integrated charge for each column of pixels along a selected exposure monitoring data line. In this embodiment the signals from the A/D's 166 occurs about every 0.1 to 10 msecs, providing a sufficiently rapid temporal sampling of the data line exposure signal to the exposure controller. During the collection phase of the exposure readout cycle (during which charge representative of radiation exposure is accumulating of the respective photodiodes in the array), the respective pixel readout switches are controlled to be in a non-conductive condition so that there is no direct conductive path between a photodiode in the array and its respective data line.

The integration time selected for the readout amplifiers 146 is determined by read and reset circuit 120 in imager processor 115. To optimize use of exposure controller 125, the readout timing (that is, the rate at which the signal from the amplifiers 146 is sampled by the sample and hold circuits 164 and digitized by the A/D's 166) is selected to be between about 0.1 and about 10 msecs. The number of times the amplifiers 162 are reset during the exposure period can vary between 1 and about 100 times. A single reset is desirable but multiple resets commonly are selected to prevent saturation of the amplifiers 162. In the multiple reset mode the amplifier output is sampled just prior to closing reset switch 162. These intermediate charge samples are summed in the exposure controller to provide a measure of the total charge accumulating on the photodiodes. The time between reset of the amplifiers 146 is typically 1 to 100 msecs. The time between reading of the A/D's is typically every 0.1 to 10 msecs. An alternate mode of operation is to digitize the output of the amplifier only once just before amplifier reset. During each frame time, these instantaneous charge-induced signals on the data lines are monitored and summed by exposure controller 125, thereby giving a nearly continuous measure of the accumulated X-ray exposure during a given collection period during which the object 114 is irradiated. Once a selected exposure level is reached (determined, as noted above, upon factors such as image quality, patient exposure, procedure times), exposure controller 125 generates a signal that is coupled to source controller 126 to cause source 112 to stop irradiation of object 114 (e.g., by turning or covering the source, or deenergizing the source).

In operation, at the start of a readout cycle controlled by imager processor 115, energy from imaging energy source 112 is applied to object 114. During the collection period of the exposure cycle, exposure signals capacitively coupled to exposure-monitoring data lines are sensed by exposure controller 125. Cumulative imaging energy exposure during a given collection period in an exposure cycle is determined based on integration of the capacitively-coupled exposure signals on the monitored data lines. The imaging energy source is controlled by exposure controller 125 to cease irradiating object 114 when a predetermined radiation exposure level has been reached. Then, the pixel readout switches are selectively closed to enable readout of charge accumulated on the radiation sensors in the array, which readout signals are processed to generate an image of the object 114.

In a further embodiment of the present invention, additional AEC structures are provided for localized areas of the for generation of signals to be used for automatic exposure control (AEC).

Figure 3:
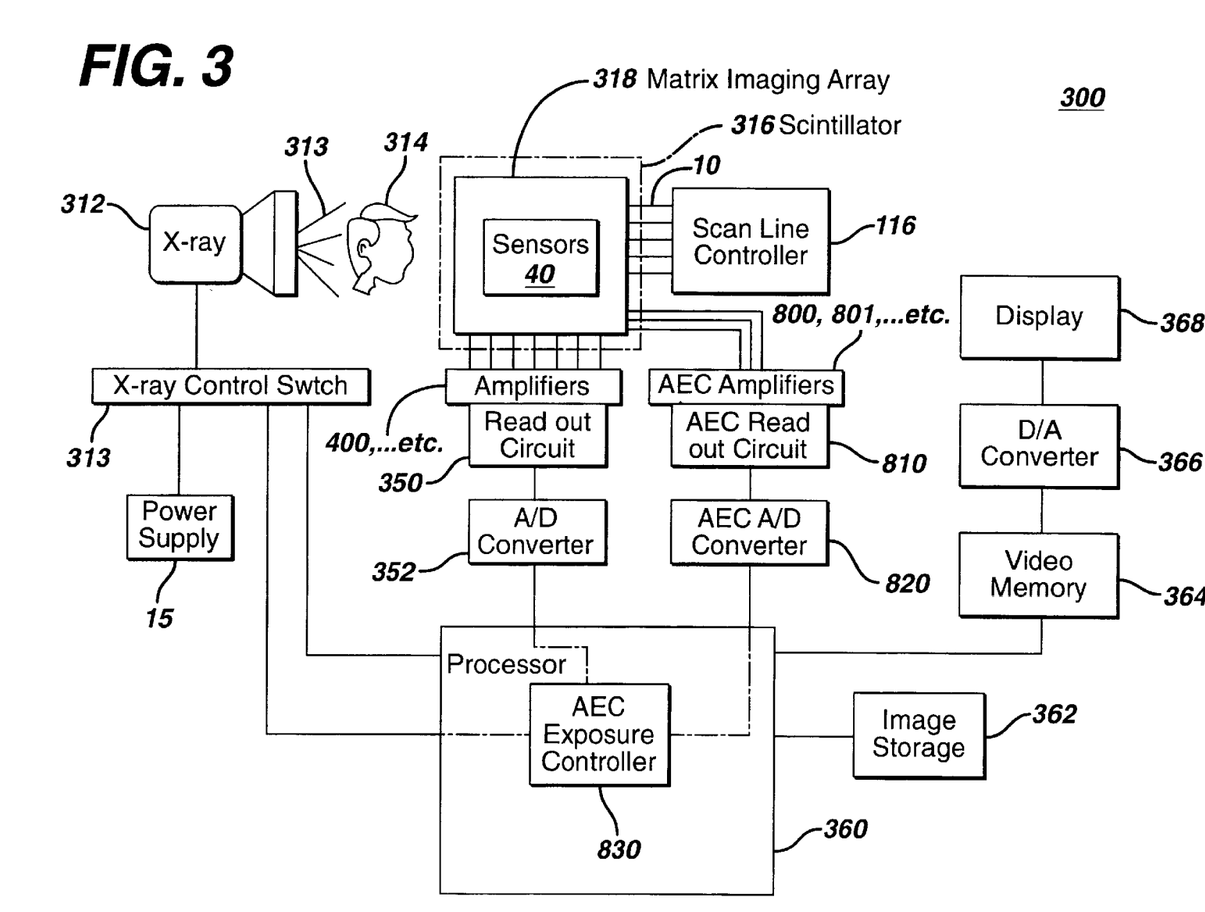
FIG. 3 is a simplified block diagram of the x-ray imaging system according to a further embodiment of the present invention.

A simplified block diagram of an X-ray imaging system 300 according to this embodiment of the present invention is illustrated in FIG. 3. An imaging energy source, for example an X-ray source 312, controlled by an X-ray control switch 314, which connects X-ray source 312 to a power supply 315, emits an x-ray irradiation field 313 toward the object (or subject) 314 to be imaged. As described above, radiation detection is commonly by means of a scintillator coupled to a photosensor array, but alternatively comprises an array of direct radiation detectors. By way of example and not limitation, the photosensor array arrangement is described herein. An x-ray radiation scintillator 316 located at the opposite side of the subject 314 from the source 312 detects x-rays which pass through the subject 314 and impinge upon a two dimensional flat panel array 318 of photosensor pixels 30 arranged as described herein. An image signal output from photosensors 31, 32 . . . , 41, 42 . . . ,etc. ., is read by respective amplifiers 400, 401, . . . etc., which are controlled by read out circuit 350, and is converted into digital data by an A/D (analog-digital) converter 354. The signal is processed by a processor 360 and then the image signal is provided to storage 362 and delivered on a demand basis to a display, typically via a video memory 364, a D/A (digital-analog) converter 366, and an image display device 368, such as a video monitor.

Further, imager 300 comprises at least one AEC amplifier 800 (and alternatively additional similar amplifiers 801, etc.) coupled to a respective AEC read out circuit 810 which is further coupled to a respective A/D converter 820. The respective coupled group of AEC amplifier 800, readout circuit 810, and converter 820 are coupled to an AEC exposure controller 830 that is typically comprised within imager processor 360. As disclosed in greater detail below, each AEC amplifier 800 is coupled to an AEC electrode disposed in the imager array so as to provide additional localized exposure information for use in control of radiation source 312. Each AEC electrode in the array 318 is typically coupled to a respective AEC amplifier.

Figure 4:
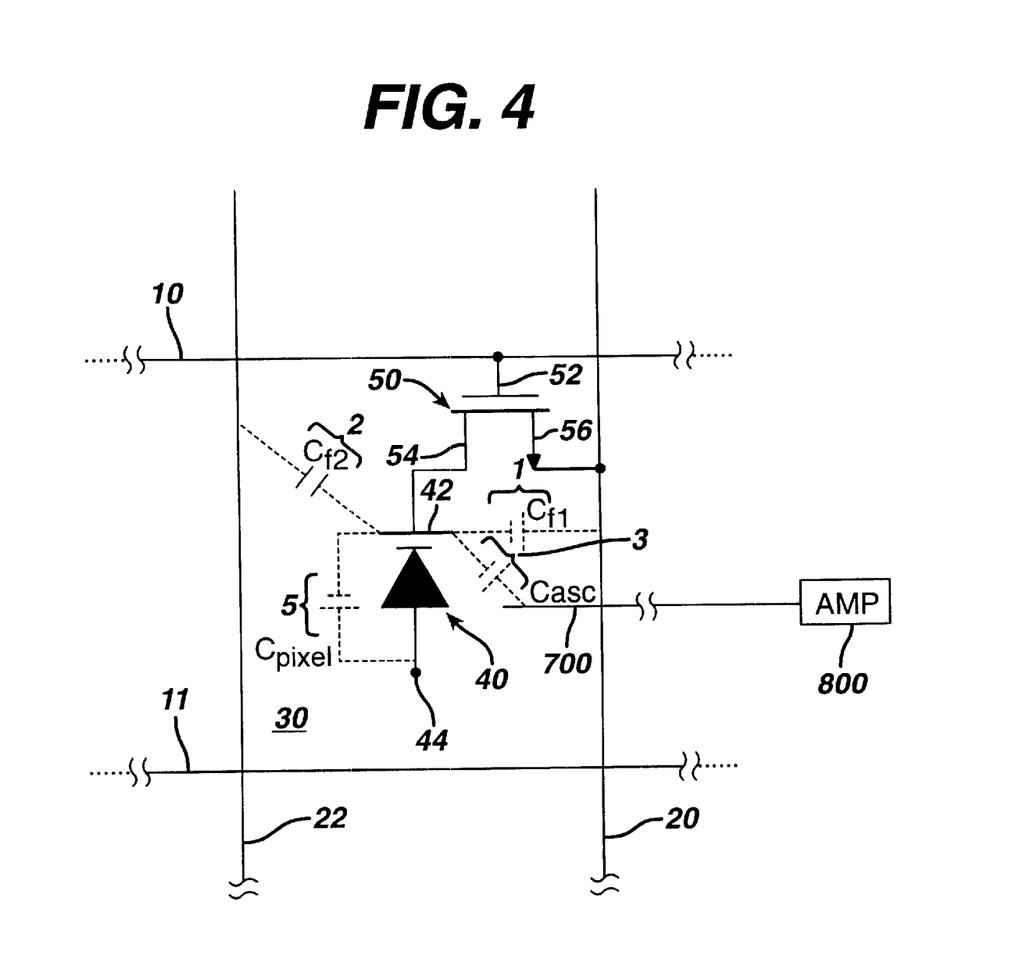
FIG. 4 is a schematic diagram of a representative pixel according to one embodiment of the present invention.

A representative photosensor pixel 30 of array 318 in accordance with this embodiment of the invention is illustrated in FIG. 4 (in FIGS. 3 and 4, solid lines represent connections made over electrical conductors and dashed lines illustrate induced coupling as described herein). Pixel 30 comprises a diode 40 having a bottom electrode 42 and connection point 44 to a common electrode (not shown) disposed over array 318. Diode 40 is coupled to a switching device 50, typically a thin film transistor (TFT) having a gate electrode 52, a drain electrode 54 coupled to diode bottom electrode 42, and a source electrode 56 coupled to a data line 20. Gate electrode 52 is connected to a scan line 10. Additionally, an AEC electrode 700 is disposed in the pixel such that a capacitance exists between diode bottom electrode 42 and AEC electrode 700. The typical width of an AEC electrode is in a range between about 2 microns and about 50 microns.

Representative capacitive coupling is also illustrated in FIG. 4, with a first fringe capacitance 1 ($C_{fringe\ 1}$, or $C_{f1}$) between diode bottom electrode 42 and a first data line 20; a second fringe capacitance 2 ($C_{fringe\ 2}$, or $C_{f2}$) between bottom electrode 42 and a second adjoining data line 22; and an AEC line fringe capacitance 3 ($C_{AEC}$) between diode bottom electrode 42 and AEC electrode 700.

As the AEC modality of this embodiment of the present invention is well adapted for providing localized AEC signals, typically only a selected number of pixels 30 within array 318 comprise AEC electrode 700, and the remainder of the pixels would correspond to the electrical representation presented in FIG. 2. The particular pixels 30 selected for use with AEC electrode 700 are determined in the design process (prior to fabrication) based upon, for example, anticipated usage of the imager and likely areas of coverage of the imager panel by the objects anticipated to be imaged.

Figure 5:
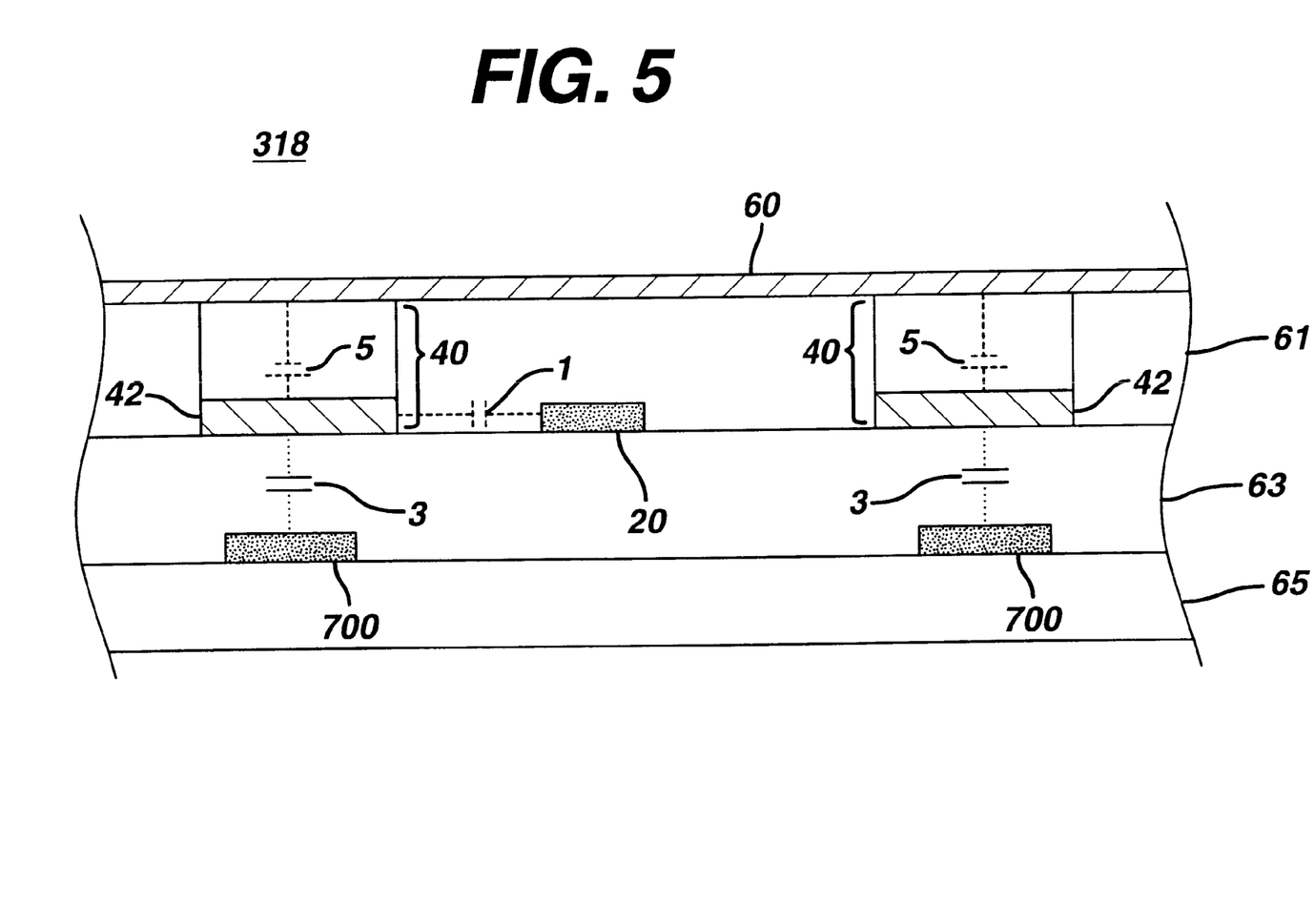
FIG. 5 illustrates a cross-sectional view of a portion of the imager according to one embodiment of the present invention.

A cross-sectional view of a representative portion of imager 318 having a pixel with and AEC electrode is presented in FIG. 5. AEC electrode is disposed over a substrate 65 on which array 318 is fabricated. As used herein, "over," "above," "under," "vertically adjacent" and the like are used to broadly describe placement of components in the structure of the array as represented in the figures, and use of such terms does not imply operational limitations with respect to orientation of the device; nor does such use imply the presence or absence of any intervening material or structure between the elements referenced.

AEC electrode is disposed on substrate 65 so as to be vertically adjacent to the diode bottom electrode 42 (which, in this arrangement, would be fabricated subsequent to formation of AEC electrode 700). A dielectric material layer 63 (typically comprising silicon nitride, silicon oxide, or a combination thereof) is disposed between AEC electrode 700 and diode bottom electrode 42. A common electrode 60, which comprises the diode top electrode, is also shown, and typically comprises a light transmissive electrical conductor such as indium tin oxide or the like. A further dielectric layer 61 surrounding diodes 40 is illustrated, as is a representation of AEC electrode capacitance 3, $C_{AEC}$, the internal capacitance 5 of diode 40, $C_{PD}$, and fringe capacitance 1, $C_{fringe\ 1}$.

In operation, radiation exposure of the array results in generation of photons that, when incident on the sensors, cause a change the charge in the diode. This change in charge is the basis for generating the readout signals from which the display image is prepared. The change also has effects the voltage of sensor bottom electrode 42, which in turn results in a parasitic capacitive coupling to other electrodes in the imager. Three parasitic capacitance of interest in the present invention are indicated in FIG. 4 as first fringe capacitance 1 $C_{f1}$ second fringe capacitance 2 $C_{f2}$, and AEC electrode capacitance 3 $C_{AEC}$. In addition, pixel diode capacitance 5 $C_{pixel}$ between diode bottom electrode 42 and diode top electrode. The pixel diode capacitance 5 is typically, by design, the largest of these capacitances noted above as the pixel diode capacitance is the principle capacitance required to store the charge generated by the radiation incident on the diode. Charge is induced on diode bottom electrode 42 due to radiation incident on the diode. This radiation typically is light from scintillator 316, or alternatively, is direct x-ray radiation interacting with the semiconductor material of the photodiode. Charge build up on diode bottom electrode 42 induces a charge in the first adjacent data line 20 and the second adjacent data line 22 through the parasitic capacitances first fringe capacitance 1 $C_{f1}$, second fringe capacitance 2 $C_{f2}$, respectively. A parasitic capacitance is also exhibited between diode bottom electrode 42 and AEC electrode 700, shown as AEC electrode parasitic capacitance 3 $C_{AEC}$. These three capacitances, $C_{f1}$, $C_{f2}$, and $C_{AEC}$ are called parasitic because they are a small fraction of the total capacitance of diode bottom electrode 42 which is dominated by the capacitance between bottom electrode 42 and the diode top electrode.

Figure 6:
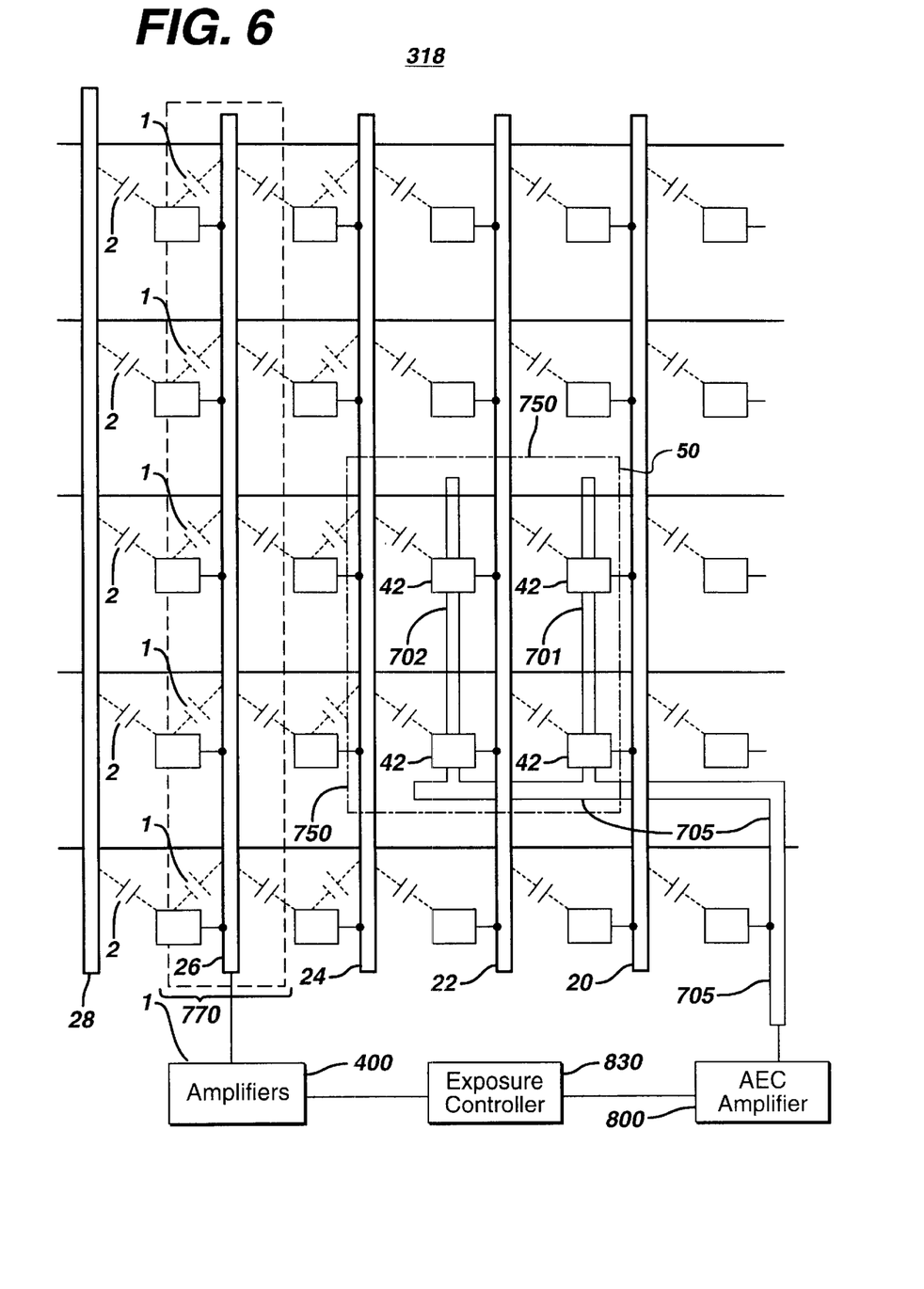
FIG. 6 is a plan view of an imager having automatic exposure control capabilities in accordance with the embodiments of the present invention.

A plan view of a portion of imager 318 comprising AEC electrodes 700 is illustrated in FIG. 6. Typically array 318 comprises a matrix of about 2300 ×1800 pixels fabricated on a 10 inch by 10 inch dielectric substrate. By way of example and not limitation, one AEC electrode receptive field region 750 comprising a representative first AEC electrode 701 and a second AEC electrode 702 is illustrated in FIG. 6. First and second AEC electrodes 701, 702 are electrically coupled to an AEC signal line 705 that serves to connect the AEC electrodes to a respective AEC amplifier 800 for each AEC electrode receptive field region 750 in the imager array 318 (a representative one of which is illustrated in FIG. 6). AEC electrodes 701 and 702 are disposed so as to underlie the respective diode bottom electrodes 42 of pixels within AEC electrode receptive field region 750 (the diode bottom electrodes 42 of pixels within AEC electrode receptive field region 750 are blackened in FIG. 6 to illustrate those pixels within region 750). While only 2 such electrodes are shown in the example group in FIG. 6, a larger number, of the order of 10 to 1000 AEC electrodes, grouped together in one or more respective AEC electrode receptive field regions 750 would be advantageous to produce a readily measurable signal and to provide a signal representative of average exposure value over a larger region of the imager 318. Similarly, multiple receptive fields could be used to obtain information on the spatial distribution of incident x-rays over the imager.

The AEC capacitive coupling 3 between AEC electrode 700 and an overlying diode bottom electrode 42, for a 5 $\mu$m wide AEC electrode width, is typically about 0.03 pF in an imaging array (the exact amount of the capacitance, of course, is a function of the thickness of the intervening dielectric material 63 between the AEC electrode and the diode bottom electrode). The first fringe parasitic capacitance 1 (between the bottom electrode 42 and data line 20 (FIG. 4)) is typically about 0.005 pF. When the electrical potential of diode bottom electrode 42 changes due to X-ray exposure, a charge is coupled to the adjacent data lines 20, 22 as well as the AEC electrodes 700. The ratio of this coupled charge to the charge induced on the photo diode for this typical coupling capacitance is given by the relation $C_f/C_{pixel}$. The pixel capacitance $C_{pixel}$ is ~0.5 pf, so the typical coupling ratios are in the range of 1 to 6%.

A representative AEC electrode receptive field region is electrically coupled to a subset of the all the pixels on the array; by way of example and not limitation, a fraction of the total number pixels in array 318 of about 1/256 the total would be comprised in a respective AEC electrode receptive field region. Given that a standard matrix array 318 includes rows and columns on the order of 2300×1800, or about 4.14 million photo diodes, then 1/256 of the total area corresponds to approximately 16,900 photodiodes. For each of these photodiodes, roughly 6% of the available signal is capacitively coupled to an associated AEC electrode 700, and therefore, the net response in such an AEC electrode receptive field would be (0.06)×(16,000)=960 times the accumulated charge on a single photo diode, if all photo diodes are illuminated equally. After integrating the charge induced on the AEC electrodes 700 in this AEC electrode receptive field for about 800 $\mu$secs in a region of the panel exposed to a high (e.g., unattenuated by an intervening object being imaged) X-ray intensity, a signal of about 2.3 pC is obtained [(800 $\mu$secs) (3pC/sec) (960)=2.3pC] is obtained, which is easily within the range of charge amplifier know in the image art. Hence the amplifier would need to be reset about every 1 msec to avoid saturation.

AEC amplifiers 800 (that is, a respective amplifier 800 for each AEC electrode receptive field region 750 in the array) are coupled to the AEC calculator 830 (FIG. 3) in processor 360 that controls the operation of x-ray source 312. The charge sensed from respective AEC electrode receptive field regions 750 provides a localized indication of the amount of x-ray radiation that incident on that portion of the array. During normal imager operation, the readout of information from each data line column is typically done sequentially; this normal imaging mode occurs after the x-ray imaging energy source has been turned off for a given exposure. During the period the x-ray source is energized, the AEC modality of the imager is used to determine an appropriate length of the x-ray exposure, and signals from the respective AEC electrode receptive field regions are separately integrated and the calculated integrals are the typically processed AEC calculator 830 to determine the accumulated imaging energy. exposure. The imaging energy source is turned off when the accumulated imaging energy value reaches a predetermined value, such as may be selected by an operator of the imager given the particular imaging evolution being performed.

In a still further embodiment of the present invention, the AEC electrode receptive field regions described above are combined with data line exposure signal monitoring as described above. For example, as shown in FIG. 6, the AEC electrode receptive region 750 is disposed in one area of the array, and a data line exposure signal monitoring region 770 is also disposed in the array. By way of example and not limitation, data line exposure monitoring region 770 is disposed around data line 26, such that fringe capacitances between data line 26 and diode bottom electrodes of pixels on either side of data line 26 are used for AEC sensing. For clarity of illustration in FIG. 6, the diodes in pixels sensed in region 770 are darkened. In region 770 the capacitive coupling is provided by first parasitic fringe capacitance 1 $C_{f1}$, between diodes on the left side of data line 26 as shown in FIG. 6 and second parasitic fringe capacitance 2 $C_{f2}$, shown on the right side of data line 26. Data line 26 and associated first and second fringe capacitances, of course, is merely exemplary of potential data line exposure signal monitoring regions 770 that can be used with data lines in array 318. As described in more detail above, each data line, including data line 26, is coupled to readout circuit amplifiers 400 adapted to time sample the charge induced on the data line for the AEC function.

In this arrangement of an imager having both AEC electrode receptive field regions 750 and data line exposure signal monitoring regions 770, the signals from the respective regions typically but not always will be similar in magnitude. By way of example and not limitation, data line 26 is capacitively coupled to pixels on each side of the line.

Each data line typically has about 4000 neighboring pixels (2000 on each side). For the same X-ray intensity resulting in a maximum of 3pC/sec of charge generation in each, photo diode, the total coupled charge in 800 µsecs would be (800 µsecs) (3 pC/sec) (4000) (0.01)=0.096 pC. During the X-ray exposure, the instantaneous charge-induced signal on the data lines is monitored at each time interval, thereby giving a real time (that is, a quasi-continuous) measure of the instantaneous X-ray exposure in real time. Once the desired exposure level is reached, the X-ray tube is turned off.

As is evident from the above discussion and the Figures, it can be appreciated that the AEC methods associated with region 750 and 770 have differing characteristics. Data line exposure signal monitoring region 770 provides information on the average X-ray exposure along a data line, whereas AEC electrode field receptivity region 750 provides the average exposure in a local region of the image. Typically it is desired to set the exposure in the region of the image with lowest X-ray intensity. In most cases the object to be imaged does not entirely cover the imaging surface so some parts of data line region 770 will be exposed to very high X-ray intensity. With multiple AEC receptive regions 750, some number of them will typically be completely under the object being imaged. Thus the AEC exposure controller 830 can turn off the X-ray source when the smallest AEC signal reaches the desired value. It should be understood that much more complex AEC exposure calculations may be advantageous. For example the object may contain some highly absorbing regions such as metal or bone. In this case the AEC exposure controller can optimize the exposure in other regions of the image as desired. Any size and number of AEC receptive field regions can be created in this manner and used to cover the entire panel 318, if necessary. When AEC receptive field regions 750 closely associated with the area of the subject to be imaged are identified, it becomes possible to obtain total accumulated X-ray exposure represented by only the identified area.

Thus, while various embodiments of the present invention have been illustrated and described, it will be appreciated to those skilled in the art that many changes and modifications may be made there unto without departing from the spirit and scope of the invention.

What is claimed is:

1. A method of operating an imaging system including a matrix-addressed imaging panel having a plurality of radiation sensors, each sensor selectively connected via a respective pixel readout switch to a respective data line, the steps comprising:

applying imaging energy from an imaging energy source to an object;

sensing at least one data line exposure signal from an exposure-monitoring data line, wherein at least one radiation sensor is capacitively coupled to said exposure-monitoring data line with the pixel readout switches in an electrically open condition; and generating a panel exposure signal in correspondence with said sensed exposure signals on said at least one exposure-monitoring data lines.

2. The method of operating an imaging system of claim 1 wherein the imaging energy source applies X-rays, and said radiation sensors are selected from the group consisting of photosensors and direct semiconductor x-ray sensors and said pixel switches are selected from the group consisting of diodes and field effect transistors.

3. The method of operating an imaging system of claim 2 wherein each of said radiation sensors comprises a photodiode and said imaging panel further comprises a scintillator optically coupled to an array of said photodiodes.

4. The method of operating an imaging system of claim 1 further comprising the step of controlling irradiation of the object to be imaged in correspondence with said panel exposure signal.

5. The method of operating an imaging system of claim 4 further comprising the step of processing said data line exposure signals to generate said panel exposure signal.

6. The method of operating an imaging system of claim 5 further comprising the step of selecting at least one exposure monitoring data line to be monitored by an exposure controller.

7. The method of operating an imaging system of claim 6 wherein the step of selecting at least one exposure monitoring data line further comprises the step of applying a model of the object to be imaged to extract imager panel exposure information in areas of interest.

8. The method of operating an imaging system of claim 3 wherein said pixels capacitively coupled to said exposure monitoring data line comprise a column of respective exposure-monitoring data line photodiodes that are disposed to be coupled to said exposure monitoring data line by said pixel readout switches, and photodiodes in adjacent columns to the column of respective exposure-monitoring data line photodiodes.

9. The method of operating an imaging system of claim 8 further comprising the step of turning off the imaging energy source based on the exposure signals on the data lines.

10. The method of operating an imaging system of claim 4 wherein the step of controlling irradiation of the object to be imaged in correspondence with said panel exposure signal further comprises at least one of the steps of deenergizing the imaging energy source and covering said imaging energy source to block radiation passage between said source and the object to be imaged.

11. An imaging system comprising:

a matrix-addressed imaging panel having a plurality of pixels;

each of said pixels comprising at least one respective radiation sensor and at least one respective pixel readout switch disposed to selectively couple the pixel radiation sensor to a respective data line in said imaging panel; and an exposure controller coupled to at least one exposure-monitoring data line in said imaging panel, said exposure controller being configured to sense a capacitively-coupled exposure signal from at least one radiation sensor capacitively coupled to said exposure-monitoring data line and to generate a panel exposure signal corresponding to incident radiation sensed during an exposure control period when the respective pixel readout switches for said exposure-monitoring data line are in an open condition.

12. The imaging system of claim 11 wherein said radiation sensors are selected from the group consisting of photosensors, and direct semiconductor x-ray sensors detection.

13. The imaging system of claim 11 wherein said exposure controller is coupled via a readout circuit to respective ones of data lines in said imaging panel, said readout circuit comprising a respective charge amplifier for each of said data lines.

14. The imaging system of claim 11 wherein said exposure controller is configured to generate said panel exposure signal corresponding to the received exposure signals from said readout circuits, said panel exposure signal being representative of radiation exposure incident on said imaging panel during a collection period in an exposure cycle of said imaging system.

15. The imaging system of claim 11 further comprising an imaging energy source and a source controller coupled to said energy source and to said exposure controller so as to be responsive to a control signal from said exposure controller to cause said energy source to cease irradiating the object to be imaged.

16. The imaging system of claim 11 wherein the imaging energy source is an X-ray source.

17. An imaging system comprising
a matrix-addressed imaging panel having an array of photosensor pixels coupled to a scintillator;
an x-ray source coupled to a source controller and disposed to irradiate an object to be imaged disposed between said source and said imaging panel in response to signals from said source controller;
an imager controller being configured to control readout from respective photosensor pixels in said imaging panel, each of said photosensor pixels comprising a photodiode coupled to a respective data line via a respective pixel readout switch, said pixel readout switch being responsive to signals generated by said imager controller; and
an exposure controller coupled to said imager panel to selectively receive capacitively-coupled exposure signals from at least one of said data lines when said respective pixel readout switches coupled to said at least one data line are controlled to be in a non-conductive state;
said exposure controller being coupled to said source controller and configured to generate a panel exposure signal in correspondence with said capacitively-coupled exposure signals and to generate a control signal to be applied to said source controller.

18. The imager of claim 17 wherein said exposure controller is selectively coupled to said data lines via a readout circuit.

19. The imager of claim 18 wherein said readout circuit comprises means for selectively coupling signals from respective data lines to said exposure controller.

20. The imager of claim 17 wherein said exposure signals represent signal on a respective data line coupled to said data line via a fringe capacitance between said data line a photodiodes in respective columns in said imager panel disposed on either side of said data line.

21. A method of automatic exposure control for an imaging system comprising a matrix-addressed x-ray imaging panel, said imaging panel comprising a scintillator optically coupled to an array of photodiodes, each photodiode being connected via a corresponding controlled switch to a corresponding data line, said data lines being sequentially arranged, each of said controlled switches being operably controlled from a connected scan line to selectively pass a signal from the corresponding photodiode to said corresponding data line, each of said data lines being connected to a readout amplifier to provide image signals for display; said imaging system further including at least one automatic exposure control (AEC) electrode disposed adjacent to at least one of said photodiodes so as to form a respective AEC electrode receptive field, each of said AEC electrodes being connected to an exposure controller for controlling an imaging energy source, comprising:
applying x-ray imaging energy from said imaging energy source to a subject;
sensing AEC signals on the AEC electrodes, the AEC signals appearing on the AEC electrodes as a result of capacitive coupling between the photodiodes and the AEC electrodes in said respective AEC receptive fields;
determining an imaging energy exposure level based on the AEC signals sensed on the AEC electrodes;
controlling the applied imaging energy in response to the energy exposure level;
selectively closing the controlled switches to provide image signals on the data lines from the photodiodes, the photodiodes providing the image signals corresponding to components of an x-ray image representation of the subject; and
displaying the x-ray image representation of the subject based on the image signals.

22. The method of automatic exposure control of the imaging system of claim 21 wherein each of said AEC electrodes is formed as a layer of conductive material disposed vertically adjacent to a respective photodiode.

23. The method of automatic exposure control of the imaging system of claim 21 wherein selectively closing the controlled switches to provide image signals on the data lines from the photodiodes comprises:
closing controlled switches on data lines one controlled switch at a time; and
integrating the image signals sensed on the data lines to produce a separate value for each photodiode, wherein said displayed image of the subject is based on said separate value for each photodiode.

24. The method of automatic exposure control of the imaging system of claim 21 wherein the capacitive coupling of the photodiodes to respective AEC electrodes is via parasitic capacitance.

25. Apparatus for automatic exposure control of a matrix-addressed imaging panel, comprising:
an x-ray imaging energy source;
a matrix-addressed imaging panel, said panel comprising a scintillator optically coupled to an array of photodiodes; a plurality of controlled switches, each switch selectively connecting a corresponding photodiode to a corresponding data line, each controlled switch connected to a scan line to selectively pass a signal from the corresponding photodiode to an associated data line, each of said data lines being coupled to a readout amplifier to provide image signals; at least one automatic exposure control (AEC) electrode disposed adjacent to selected photodiodes so as to form at least one AEC electrode receptive field; and an AEC controller coupled to said AEC electrodes;
each of said AEC electrodes being coupled to pass AEC calculator AEC signals appearing on the AEC electrodes as a result of capacitive coupling between said photodiodes and said AEC electrodes; and
a display operably connected to the imaging array and operable to display an x-ray image responsive to the imaging array.

26. Apparatus for automatic exposure control of a matrix-addressed imaging panel of claim 25 further comprising a power supply, and a control switch operably controlling the imaging energy source, the control switch operably connected to the AEC exposure controller such that the control switch is opened and the imaging energy source is turned off responsive to an output of the AEC exposure controller.

27. Apparatus of claim 25 wherein said AEC electrodes comprise respective pluralities of AEC electrodes disposed in respective AEC electrode receptive fields, each of said respective pluralities of AEC electrodes being coupled to a respective AEC amplifier.

28. Apparatus of claim 25 wherein said at least one AEC electrode is disposed so as to be capacitively coupled to a plurality of sensors.

29. Apparatus of claim 25 wherein said at least one of said AEC electrodes has a width of about 2 microns to about 50 microns.

* * * * *